United States Patent
Sawai

(10) Patent No.: US 10,945,651 B2
(45) Date of Patent: Mar. 16, 2021

(54) AROUSAL LEVEL DETERMINATION DEVICE

(71) Applicant: DENSO CORPORATION, Kariya (JP)

(72) Inventor: Yuki Sawai, Kariya (JP)

(73) Assignee: DENSO CORPORATION, Kariya (JP)

(*) Notice: Subject to any disclaimer, the term of this patent is extended or adjusted under 35 U.S.C. 154(b) by 0 days.

(21) Appl. No.: 16/460,116

(22) Filed: Jul. 2, 2019

(65) Prior Publication Data

US 2020/0008732 A1    Jan. 9, 2020

(30) Foreign Application Priority Data

Jul. 5, 2018  (JP) .............................. JP2018-128257
Jun. 7, 2019  (JP) .............................. JP2019-107255

(51) Int. Cl.

| | | |
|---|---|---|
| G08B 23/00 | (2006.01) | |
| A61B 5/18 | (2006.01) | |
| G08B 21/06 | (2006.01) | |
| B60K 28/06 | (2006.01) | |
| A61B 5/00 | (2006.01) | |
| A61B 5/11 | (2006.01) | |

(52) U.S. Cl.
CPC ............. A61B 5/18 (2013.01); B60K 28/06 (2013.01); G08B 21/06 (2013.01); *A61B 5/1118* (2013.01); *A61B 5/7405* (2013.01)

(58) Field of Classification Search
CPC ....... A61B 5/1118; A61B 5/18; A61B 5/7405; B60K 28/06; G08B 21/06
USPC ....................................................... 340/576
See application file for complete search history.

(56) References Cited

U.S. PATENT DOCUMENTS

| | | | |
|---|---|---|---|
| 6,335,689 B1* | 1/2002 | Mine ...................... | B60K 28/06 |
| | | | 180/272 |
| 10,562,412 B1* | 2/2020 | Main .................... | A61B 5/6893 |
| 2013/0328684 A1* | 12/2013 | Chang .................. | B62D 15/029 |
| | | | 340/575 |
| 2014/0142867 A1* | 5/2014 | Shirakata ................ | G01P 13/00 |
| | | | 702/33 |
| 2015/0105976 A1* | 4/2015 | Shikii .................... | B60K 35/00 |
| | | | 701/36 |
| 2015/0216466 A1 | 8/2015 | Kronberg et al. | |
| 2017/0096063 A1* | 4/2017 | Jang ...................... | B60K 28/066 |
| 2018/0033280 A1* | 2/2018 | Taylor ............... | G06K 9/00288 |
| 2018/0220948 A1* | 8/2018 | Kojima ................ | A61B 5/7278 |
| 2019/0299999 A1* | 10/2019 | Liu ........................ | B60W 40/08 |

FOREIGN PATENT DOCUMENTS

| | | |
|---|---|---|
| JP | 2010-204984 A | 9/2010 |
| JP | 2013-156707 A | 8/2013 |
| JP | 2014-092965 A | 5/2014 |
| JP | 2017-194772 A | 10/2017 |
| JP | 2017-217472 A | 12/2017 |

\* cited by examiner

*Primary Examiner* — Naomi J Small
(74) *Attorney, Agent, or Firm* — Maschoff Brennan

(57) ABSTRACT

An arousal level determination device, which determines an arousal level of a driver driving a vehicle, includes a detection part and a determination part. The detection part is configured to detect an amount of body movement indicating a magnitude of movement of a body of the driver. The determination part is configured to determine the arousal level of the driver. The determination part determines that the driver is in an initial stage of decline in the arousal level when the amount of body movement has a decreasing trend.

10 Claims, 10 Drawing Sheets

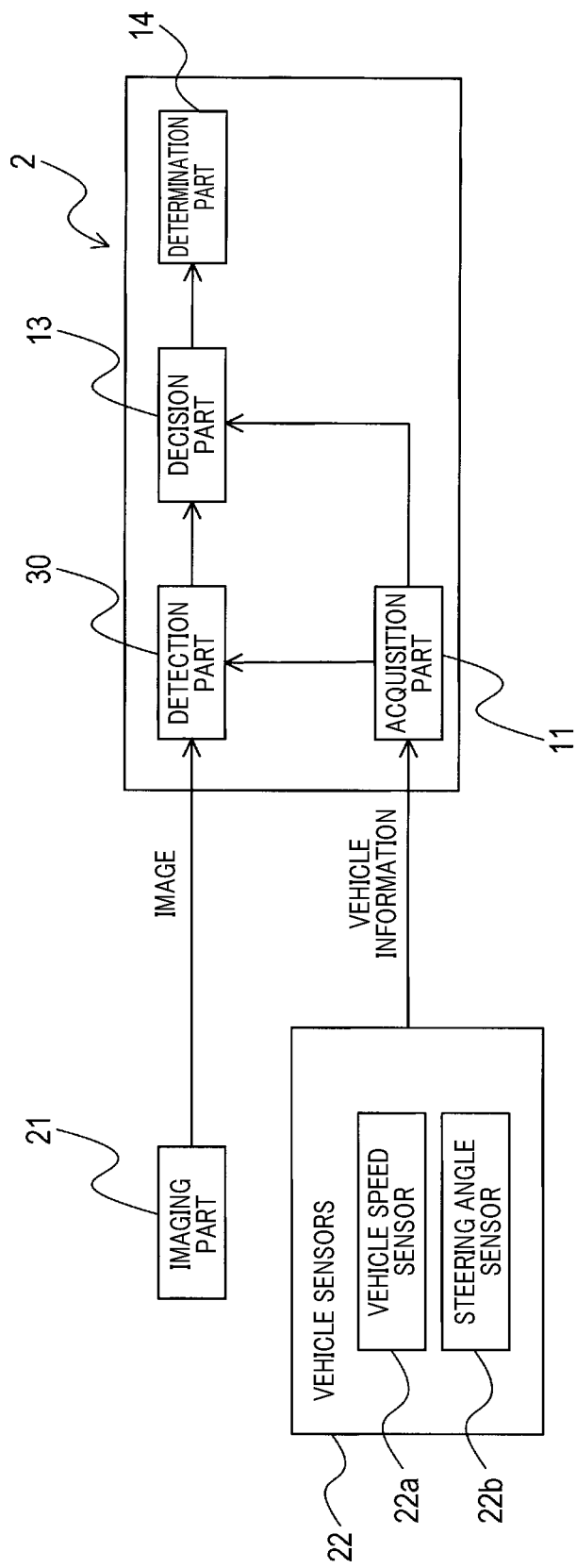

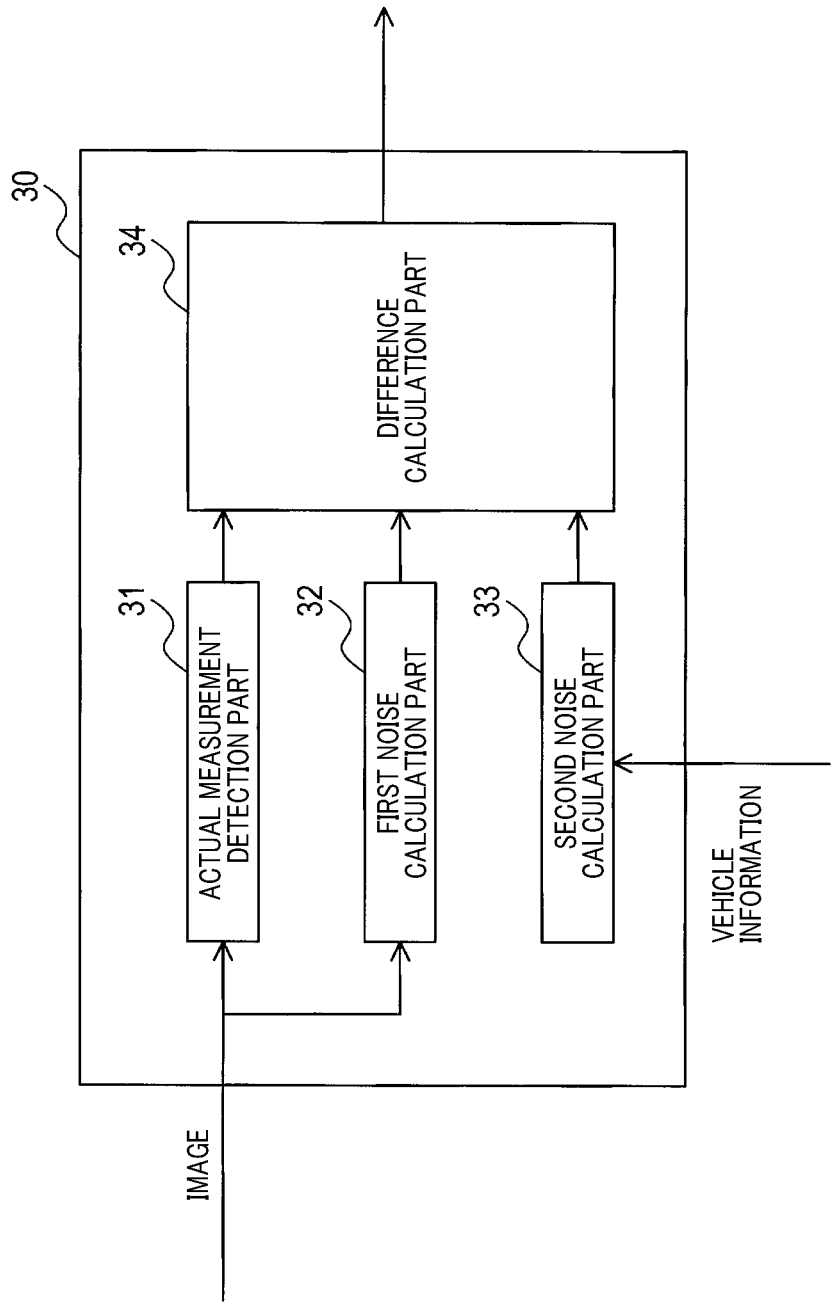

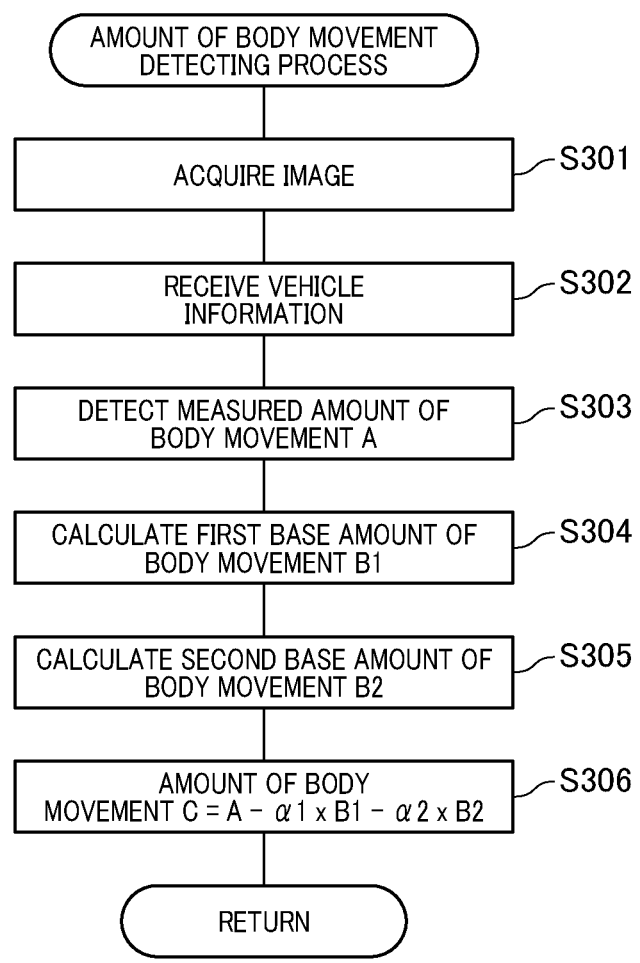

AROUSAL LEVEL DETERMINATION DEVICE

CROSS-REFERENCE TO RELATED APPLICATION

This application is based on and claims the benefit of priority from earlier Japanese Patent Application No. 2018-128257 filed Jul. 5, 2018, and No. 2019-107255 filed Jun. 7, 2019, the descriptions of which are incorporated herein by references.

TECHNICAL FIELD

The present disclosure relates to an arousal level determination device that determines an arousal level of a driver driving a vehicle.

BACKGROUND

There are devices that determine decline in an arousal level of a driver for detecting a forestate of drowsy driving of the driver driving a vehicle.

Conventionally, method of detecting decline in an arousal level from temporal changes of subsidiary movements such as hand movement, neck movement, sighing, deep breathing, and yawning is known. This is based on findings that while a frequency of such subsidiary movements increases because a driver makes an effort to be aroused as much as possible along with the decline in an arousal level, the frequency of the subsidiary movements decreases when the arousal level further lowers due to sleepiness.

SUMMARY

One aspect of the present disclosure is an arousal level determination device which determines an arousal level of a driver driving a vehicle and includes a detection part and a determination part. The detection part is configured to detect an amount of body movement indicating a magnitude of movement of a body of the driver. The determination part is configured to determine the arousal level of the driver. The determination part determines that the driver is in an initial stage of decline in the arousal level when the amount of body movement is declining.

BRIEF DESCRIPTION OF THE DRAWINGS

In the accompanying drawings:

FIG. 6 is a block diagram showing a configuration of an arousal level determination device according to a second embodiment;

FIG. 7 is a block diagram showing a configuration of a detection part of the second embodiment;

FIG. 10 is a diagram showing an example of a processing procedure of detecting the amount of body movement according to the second embodiment.

DETAILED DESCRIPTION OF THE PREFERRED EMBODIMENTS

In order to suppress drowsy driving from occurring, it is desirable to detect decline in an arousal level of a driver as soon as possible. However, the detailed study by the inventor reveals that the method known conventionally is not adequate to detect an initial stage of decline in the arousal level. That is, the subsidiary movements occur as waking efforts because the driver feels very drowsy and tries to fight sleepiness. Therefore, it is considered that the arousal level of the driver significantly lowers already at a stage where the frequency of the subsidiary movements becomes high.

An embodiment of the present disclosure provides an arousal level determination device capable of detecting an initial stage of decline in an arousal level.

One aspect of the present disclosure is an arousal level determination device which determines an arousal level of a driver driving a vehicle and includes a detection part and a determination part. The detection part is configured to detect an amount of body movement indicating a magnitude of movement of a body of the driver. The determination part is configured to determine the arousal level of the driver. The determination part determines that the driver is in an initial stage of decline in the arousal level when the amount of body movement has a decreasing trend.

With such a configuration, it is possible to detect decline in the arousal level of the driver at a stage earlier than a stage in which a frequency of the subsidiary movements becomes high.

An embodiment of the present disclosure will be described below with reference to drawings.

1. First Embodiment

[1-1. Configuration]

Figure 1:
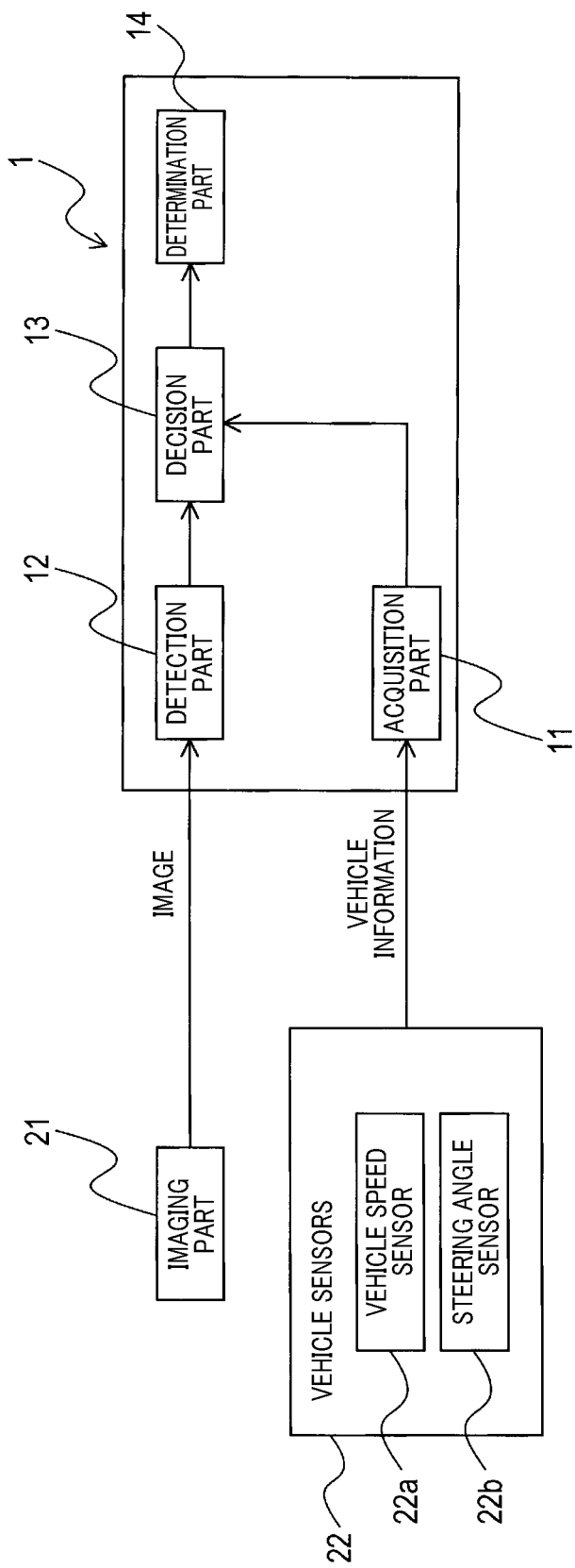
FIG. 1 is a block diagram showing a configuration of an arousal level determination device according to a first embodiment.

An arousal level determination device 1 shown in FIG. 1 is a device mounted on a vehicle such as an automobile for determining an arousal level of a driver driving the vehicle.

In addition to the arousal level determination device 1, an imaging part 21 and a vehicle sensor 22 are mounted on the vehicle on which the arousal level determination device 1 is mounted.

The imaging part 21 is provided at a front in a vehicle compartment at a position facing a driver's seat and configured to capture an image of a driver seated on the driver's seat from the front. The imaging part 21 is capable of capturing an image of the driver along a time series. That is, the imaging part 21 is capable of capturing an image of the driver every predetermined time. A camera can be exemplified as the imaging part 21.

The vehicle sensor 22 detects vehicle information such as a traveling state information on of a vehicle and an operation information for the vehicle. The vehicle information detected by the vehicle sensor 22 is used for processing in a decision part 13 described later. In the present embodiment, a vehicle speed sensor 22a for detecting a running speed of the vehicle is included as the vehicle sensor 22 for detecting a traveling state information on of the vehicle. In addition, in the present embodiment, a steering angle sensor 22b for detecting a steering angle of a steering is included as the other vehicle sensor 22 for detecting an operation to the vehicle.

The arousal level determination device 1 is constituted mainly of a microcomputer including a CPU, a RAM, a ROM, an I/O interface, and bus lines connecting these components, etc., and executes various processing. The arousal level determination device 1 includes, as shown in FIG. 1, an acquisition part 11, a detection part 12, the decision part 13, and a determination part 14 as functional blocks realized by executing a program stored in the ROM, that is, as virtual constituent elements. Methods for realizing functions of respective parts included in the arousal level determination device 1 are not limited to software, but a part or all of the functions may be realized by using one or more hardware components. For example, when the above-described functions are realized by an electronic circuit as hardware, the electronic circuit may be realized by a digital circuit, an analog circuit, or a combination thereof.

The acquisition part 11 is configured to acquire vehicle information detected by the vehicle sensor 22. The acquisition part 11 acquires the vehicle information directly from the vehicle sensor 22 or through an in-vehicle network such as CAN (Registered Trademark).

The detection part 12 is configured to detect an amount of body movement of a driver. The amount of body movement is a value indicating a magnitude of the amount of body movement of body movement detected in the detection part 12 is used for determining an arousal level of the driver in a determination part 14 described later. The detection part 12 performs differential processing on an image obtained from the imaging part 21 to detect an amount of movement of a driver on the image as the amount of body movement.

Specifically, the detection part 12 first acquires an image from the imaging part 21.

Figure 2:
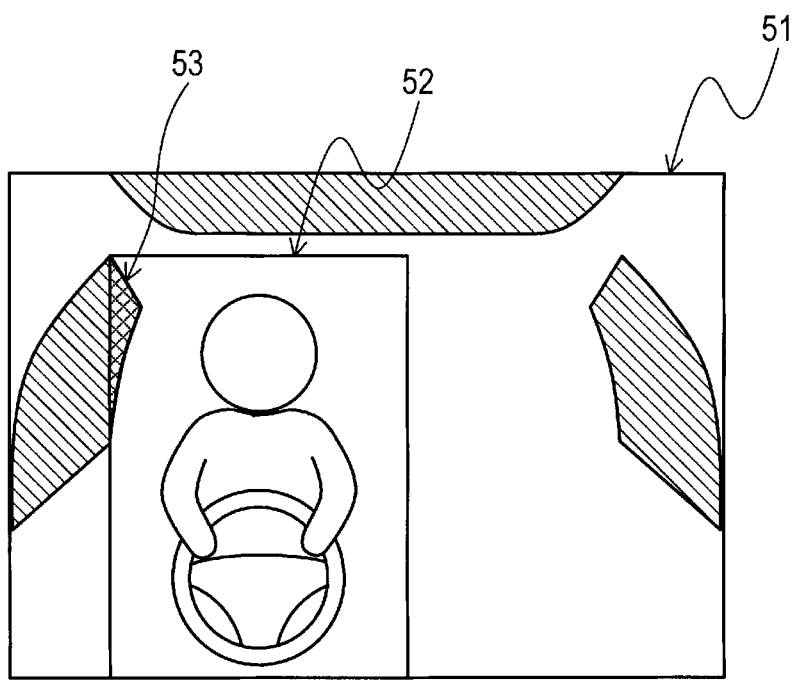
FIG. 2 is a diagram showing a detection range of an amount of body movement in an image.

Then, as shown in FIG. 2, the detection part 12 extracts a driver and its peripheral portion on an acquired image 51 as a detection range 52. At this time, it is preferable that the upper half of the driver is included in the detection range 52 so that movement of at least an arm and a head of the driver can be detected. Further, the detection range 52 is preferably wider than the minimum range in which the driver properly seated on the driver's seat can be detected so that the movement of the driver is detected within the detection range 52, and it is preferable to extract also its peripheral region of the driver as the detection range 52. The detection range 52 may be a range in which a range obtained experimentally so that the movement of the driver that can be detected is set in advance or a range which is appropriately set on site so that the detection range 52 may be changed for each driver. On the other hand, a region which a moving body other than the driver which is possibly included in the detection range 52 enters within a background, for example, a region in a window frame next to the driver's seat, a region in a window frame of the rear seat, or the like, is excluded from the detection range 52 as an excluded region 53.

Then, the detection part 12 performs differential processing between a detection range in an image captured at a predetermined clock time and a detection range in an image captured at one clock time before the clock time to extract a region which has changed in the detection ranges between the both images. The detection part 12 calculates an area of a region which is considered to have changed due to the movement of the driver for a pixel group identified as changed regions and defines the area as an amount of body movement. As the changed regions, noise due to reasons such as fluctuation of brightness may be detected, a movement of a person behind the driver's seat, a person on a passenger seat, and the like may be detected. However, it is possible to extract a region caused by the movement of the driver from among the changed regions by considering a position and a size of the driver as a main detection target.

The decision part 13 is configured to decide whether the determination part 14 determines an arousal level. In the present embodiment, the decision part 13 is configured to decide whether to use the amount of body movement supplied by the detection part 12 for the determination of the arousal level in the determination part 14. That is, the decision part 13 decides whether the determination part 14 determines the arousal level for the amount of body movement supplied by the detection part 12. In addition, the decision part 13 decides whether the determination part 14 determines the arousal level based on the vehicle information input by the acquisition part 11. In the present embodiment, it is decided whether the determination part 14 determines the arousal level based on the vehicle speed detected by the vehicle speed sensor 22a and the steering angle detected by the steering angle sensor 22b. Processing in the decision part 13 will be described later in detail.

The determination part 14 is configured to determine the arousal level. Specifically, it determines that the driver is in an initial stage of decline in an arousal level when the amount of body movement has a decreasing trend. This is based on a relation between an arousal level and the amount of body movement of the driver, which was found by the present inventor.

The present inventor estimated an arousal level of a driver according to the method described in the literature (that is, "Prediction of Automobile Driver Sleepiness (1st Report, Rating of Sleepiness Based on Facial Expression and Examination of Effective Predictor Indexes of Sleepiness)", KITAJIMA Hiroki and others, Transactions of the Japan Society of Mechanical Engineers. C, vol. 63, No. 613. PP 93-100, 1997), and investigated the relation between an arousal level and the amount of body movement of the driver. Specifically, the present inventor estimated the arousal level of the driver by five stages of a sleepiness level 0 to a sleepiness level 4 described in the above literature, that is, with a standard of five stages: a sleepiness level 0; "looks not sleepy at all", a sleepiness level 1; "looks slightly sleepy", a sleepiness level 2; "looks sleepy", a sleepiness level 3; "looks quite sleepy", and a sleepiness level 4; "looks extremely sleepy".

As a result, in a transitional stage of the sleepiness level 0 to the sleepiness level 2, it is found that the amount of body movement of a driver tends to decrease as the sleepiness level rises. It is thought that this is due to occurrence of unconscious slowdown of body movement of the driver by decline of the arousal level. On the other hand, at a stage of sleepiness level 3 or higher where the arousal level has decreased, the amount of body movement tends to increase. It is thought that this is because the driver becomes aware of sleepiness and makes conscious waking efforts, and thereby various body movements are exhibited.

Based on such a finding, the arousal level determination device 1 of the present embodiment determines that the driver is in an initial stage of decline in the arousal level when the amount of body movement has a decreasing trend. Further, the arousal level determination device 1 determines that the driver is in a progressive stage of decline in the arousal level when the amount of body movement is changed from a decreasing trend to an increasing trend. The processing in the determination part 14 will be described later in detail.

[1-2. Processing]

The processing executed by the arousal level determination device 1 will be described with reference to flowcharts in FIGS. 3 and 4.

First, the processing shown in FIG. 3 will be described. The processing of FIG. 3 is executed repeatedly at every predetermined time after an ignition switch of a vehicle is turned on.

First, at S101, the arousal level determination device 1 detects the amount of body movement. Here, S101 corresponds to the processing as the detection part 12.

Subsequently, the arousal level determination device 1 performs the processing of S102 to S105. S102 to S105 corresponds to the processing as the decision part 13.

First, at S102, the arousal level determination device 1 determines whether the vehicle is in a traveling state. When it is determined that the vehicle is in a traveling state at S102, the processing of the arousal level determination device 1 proceeds to S103. On the other hand, when it is determined that the vehicle is not in a traveling state at S102, the processing of the arousal level determination device 1 proceeds to S105 and terminates the processing of FIG. 3 after deciding not to use the amount of body movement detected by the detection part 12 for the determination of the arousal level in the determination part 14.

That is, when the vehicle is not in the traveling state and is stopped, the arousal level determination device 1 decides not to use the amount of body movement detected by the detection part 12 for the determination of the arousal level. This intends to extract only the amount of body movement of the driver during driving. When the vehicle is stopped, the attention of the driver is diverted from driving and the driver may exhibit another behavior such as handling a baggage placed on a passenger seat. Therefore, the detected amount of body movement may reflect movement of a body due to other movement other than movement of the body caused by decline in the arousal level. Thus, in the present embodiment, when the vehicle is not in the traveling state, the detected amount of body movement is not used for the determination of the arousal level. Note that, in the present embodiment, whether the vehicle is in the traveling state is determined based on whether the vehicle speed is equal to or less than zero.

Subsequently, at S103, the arousal level determination device 1 determines whether the steering angle is equal to or less than a threshold value. Specifically, when a reference steering angle, which is a steering angle in a straight-traveling state, is 0, it is determined whether the magnitude of the steering angle relative to the reference steering angle, in other words, the absolute value of the steering angle, is less than a predetermined threshold value. That is, it is determined whether the steering angle is within a predetermined range including the reference steering angle in S103. When the arousal level determination device 1 determines that the steering angle is equal to or less than the threshold value in S103, the processing proceeds to S104, decides to use the amount of body movement detected by the detection part 12 for the determination of the arousal level, and then terminates the processing of FIG. 3. On the other hand, when the arousal level determination device 1 determines that the steering angle is not equal to or less than the threshold value in S103, in other words, it is determined that the steering angle is larger than the threshold value, the process proceeds to S10, decides not to use the amount of body movement detected by the detection part 12 for the determination of the arousal level, and terminates the processing of FIG. 3.

That is, the arousal level determination device 1 decides not to use the detected amount of body movement for the determination of the arousal level when the steering angle is larger than the threshold value. This intends to exclude a large body movement caused by a steering operation. For example, when making a right turn or left turn, the driver sometimes turns a steering wheel greatly and thus the arm of the driver moves greatly. For this reason, the detected amount of body movement sometimes reflects movement of the body caused by the steering operation. Thus, in the present embodiment, whether movement of the body is caused by the steering operation is determined by the steering angle, and when the steering operation is large, the amount of body movement detected during this period is not used for the determination of the arousal level.

Figure 5:
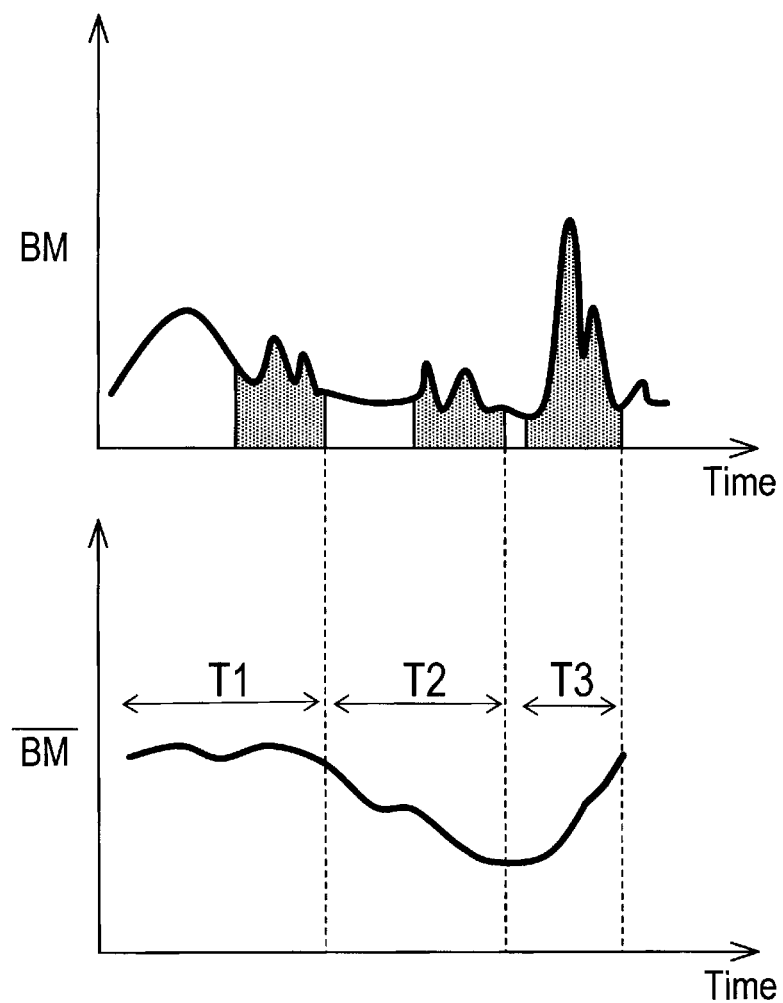
FIG. 5 includes a diagram showing changes of the amount of body movement of a driver and a diagram showing changes of its average amount of body movement.

The amount of body movement BM decided to be used for the determination of the arousal level at S104 is stored as a time-series amount of body movement as shown in FIG. 5. Then, the time-series amount of body movement is converted into an average amount of body movement per unit time (called BM bar). A change trend of the amount of body movement can be easily detected by converting the time-series amount of body movement into the average amount of body movement per unit time. The unit time mentioned here is a value set so that the change trend of the amount of body movement can be properly obtained and can be experimentally calculated in advance.

Next, the processing shown in FIG. 4 will be described. The processing of FIG. 4 is a processing of determining the arousal level based on the amount of body movement detected by the detection part 12. The processing of FIG. 4 is repeatedly executed for each predetermined time after the ignition switch is turned on. The processing of FIG. 4 corresponds to the processing as the determination part 14.

The contents of processing of FIG. 4 will be described with reference to FIG. 5. As shown in the time-series average amount of body movement of FIG. 5, a period T1 is a period during which the amount of body movement is in a constant trend and a driver is arouse (called an aroused stage). The arousal level of the driver in the aroused stage is "looks not sleepy at all" of the sleepiness level 0 according to the above standard. At the sleepiness level 0, upper eyelids of the driver are open, and an eye-blink speed is fast. When the arousal level of the driver decreases from this stage, the amount of body movement starts to decrease. It is thought that this is due to occurrence of unconscious slowdown of body movement of the driver by decline of the arousal level. A period T2 is a period during which the amount of body movement is in the decreasing trend. This stage is a stage at which the driver starts to become sleepy unconsciously, that is, an initial stage of decline in the arousal level. The arousal level of the driver in the initial stage is "looks slightly sleepy" of the sleepiness level 1 to "looks sleepy" of the sleepiness level 2. At the sleepiness level 1 to the sleepiness level 2, the upper eyelids of the driver sag or the eyes are half-open. Further, a period of fast eye-blink speed and a period of slow eye-blink speed also co-exist. When the arousal level further decreases from this stage, the amount of body movement is changed from a decreasing trend to an increasing trend. It is thought that this is because the driver becomes aware of sleepiness and makes conscious waking efforts, and thereby various body movements are exhibited. A period T3 is a period during which after the amount of body movement is changed from a decreasing trend to an increasing trend, it is continuously in the increasing trend. This stage is a stage at which the arousal level of the driver greatly decreases, and the driver is sleepy, that is, a progressive decline stage in the arousal level. The arousal level of the driver in the progress stage is "looks quite sleepy" of the sleepiness level 3. At the sleepiness level 3, the eyes of the driver are almost closed, the upper eyelids hang down to pupils, and the eye-blink speed is slow.

The determination part 14 determines that the driver is in the initial stage of decline in the arousal level when the amount of body movement of the driver is in the decreasing trend as in the period T2. Further, the determination part 14 determines that the driver is in the progressive decline stage in the arousal level when the amount of body movement is changed from the decreasing trend to the increasing trend, that is, when the period T2 has passed and the period T3 starts.

Figure 4:
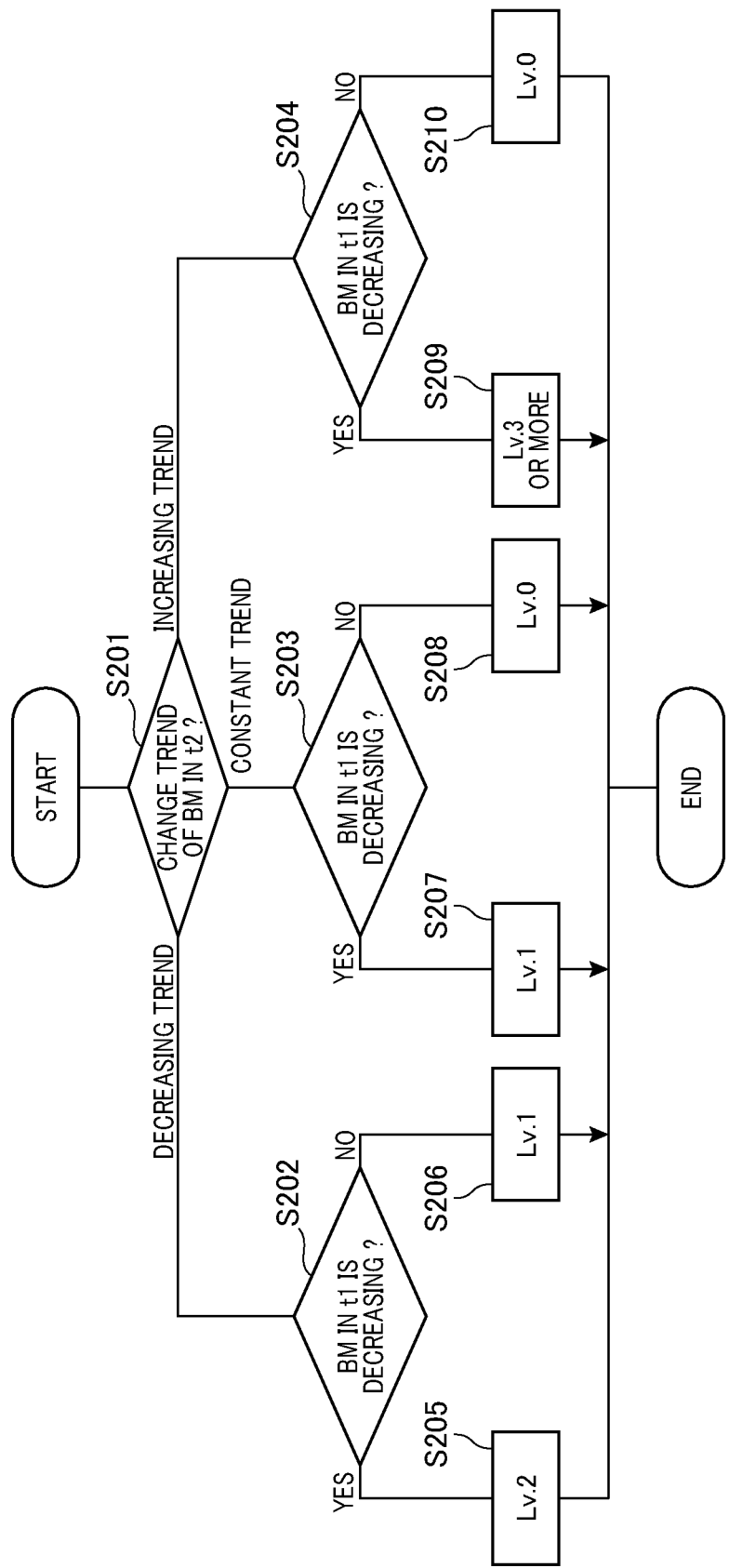
FIG. 4 is a diagram showing another example of a processing procedure in the arousal level determination device.

The processing of FIG. 4 is performed specifically as follows.

First, at S201, the arousal level determination device 1 determines whether the amount of body movement in a past predetermined period t2 is in the decreasing trend, the constant trend, or the increasing trend. The decreasing trend means a state in which the amount of body movement decreases in the long term. A temporary decrease does not always lead to the decreasing trend, and inversely even a temporary increase may lead to a decreasing trend. For example, the differences between average amount of body movements continuous in time series are calculated, and whether it is in the decreasing trend may be determined based on conditions such as a percentage of the average amount of body movements indicating decrease, the number of continuous amount of body movements indicating decrease, and a degree of decrease in a predetermined period. The same applies to the increasing trend as well. If the amount of body movement does not correspond to any of the decreasing trend and the increasing trend, it may be determined to be a constant trend.

When it is determined in S201 that the amount of body movement is in the decreasing trend, the processing of the arousal level determination device 1 proceeds to S202. In this case, it is estimated that the arousal level of the driver is in the period T2 in FIG. 5, that is, in the initial stage of decline in the arousal level.

Subsequently, at S202, the arousal level determination device 1 determines whether the amount of body movement in a predetermined period t1 one period before the predetermined period t2 is in the decreasing trend. When it is determined at S202 that the amount of body movement in the predetermined period t1 one period before is in the decreasing trend, the processing of the arousal level determination device 1 proceeds to S205, determines that the arousal level of the driver is the sleepiness level 2, and then terminates the processing of FIG. 4. In this case, since the decreasing trend continues during the periods t1 and t2, it is estimated that the driver is in a stage of a low arousal level also in the initial stage of decline in the arousal level. On the other hand, when it is determined that at S202 that the amount of body movement in the predetermined period t1 one period before is not in the decreasing trend, the processing of the arousal level determination device 1 proceeds to S206, determines that the arousal level of the driver is the sleepiness level 1, and then terminates the determination processing of FIG. 4. In this case, since the amount of body movement is not in the decreasing trend in the period t1, it is estimated that the driver is in a stage of a high arousal level also in the initial stage of decline in the arousal level.

On the other hand, when it is determined at S201 that the amount of body movement in the predetermined period t2 is in the constant trend, the processing of the arousal level determination device 1 proceeds to S203 and determines whether the amount of body movement in the predetermined period t1 one period before the predetermined period t2 is in the decreasing trend.

When it is determined at S203 that the amount of body movement in the predetermined period t1 one period before is in the decreasing trend, the processing of the arousal level determination device 1 proceeds to S207 and determines that the arousal level of the driver is the sleepiness level 1, and then terminates the processing of FIG. 4. In this case, since the amount of body movement is in the decreasing trend in the period t1, it is estimated that the arousal level of the driver is in the period T2 in FIG. 5, that is, in the initial stage of decline in the arousal level. However, since the decreasing trend settled in the subsequent period t2, it is estimated that the driver is in a stage of a low arousal level, that is, in the sleepiness level 1 also in the initial stage of decline in the arousal level.

On the other hand, when it is determined at S203 that the amount of body movement in the predetermined period t1 one period before is not in the decreasing trend, the processing of the determination device 1 proceeds to S208 and determines that the arousal level of the driver is the sleepiness level 0, and then terminates the processing of FIG. 4. In this case, it is estimated that the arousal level of the driver is in the period T1 in FIG. 5, that is, in the aroused stage. Furthermore, when it is determined at S201 that the amount of body movement in the predetermined period t2 is in the increasing trend, the processing of the arousal level determination device 1 proceeds to S204 and determines whether the amount of body movement in the predetermined period t1 one period before the predetermined period t2 is in the decreasing trend.

When it is determined at S204 that the amount of body movement in the predetermined period t1 one period before is in the decreasing trend, the processing of the arousal level determination device 1 proceeds to S209 and determines that the arousal level of the driver is the sleepiness level 3 or more, and then terminates the processing of FIG. 4. In this case, it is estimated that the arousal level of the driver is in the period T3 in FIG. 5, that is, a progressive decline stage of arousal level. When it is determined at S209 that the arousal level of the driver is the sleepiness level 3 or more, repetition of the processing of FIG. 4 is interrupted, and the vehicle takes action to urge the driver to be aroused. Examples of the action taken by the vehicle include informing the driver of decline in the arousal level by sound and evacuating to a road shoulder by automated driving. The arousal level determination device 1, after confirming that the driver is aroused, restarts the interrupted processing of FIG. 4.

On the other hand, when it is determined at S204 that the amount of body movement in the predetermined period t1 one period before is not in the decreasing trend, the processing of the arousal level determination device 1 proceeds to S210 and determines that the arousal level of the driver is the sleepiness level 0, and then terminates the processing of FIG. 4. In this case, it is estimated that the arousal level of the driver is in the period T1 in FIG. 5, that is, in the aroused stage.

[1-3. Effects]

According to the embodiment described above in detail, the following effects can be obtained.

(1a) Since the amount of body movement of the driver is detected to be in the decreasing trend, the decline in the arousal level of the driver can be detected at a stage earlier than a stage in which the frequency of the subsidiary movement becomes high.

(1b) Individual difference in appearance of the subsidiary movement, such as yawn caused as a result of the waking effort of the driver, is large, and in a case of a person who is less likely to cause the subsidiary movement defined in advance, there is a possibility of overlooking decline in the arousal level. In the present embodiment, since the arousal level is determined by use of the amount of body movement that totally captures the movement of the body, even an undefined subsidiary movement can be detected as movement of the body.

(1c) Other methods for determining the arousal level include methods of capturing a facial image of the driver and calculating an eye-closing rate from the movement of eyelid and detecting yawning from the movement of the mouth. However, when the driver wears sunglasses or a mask, it is impossible to recognize the movement of the eyelid or mouth by the image with these methods, thus making it difficult to determine the arousal level. In contrast, according to the present embodiment, the arousal level of the driver of various body shapes can be determined.

(1d) The accuracy of determination of the arousal level can be increased by not determining the arousal level when the vehicle is not in the traveling state.

(1e) The accuracy of determination of the arousal level can be increased by not determining the arousal level when the steering angle is larger than the threshold value.

(1f) The arousal level of the driver can be determined at multiple stages according to the change trend of the amount of body movement. The determination results at multiple stages can be used for various methods of arousing the driver according to the stages. For example, when the arousal level of the driver is determined to be the sleepiness level 1 to sleepiness level 2, it may be considered to arouse the driver by gentle intervention on the vehicle side, such as supplying a gentle cold wind to the driver. In contrast, when the arousal level of the driver is determined to be the sleepiness level 3 or more, it may be considered to aggressively arouse the driver, for example, by warning the driver by sound.

2. Second Embodiment

[2-1. Configuration]

The basic configuration of the second embodiment is the same as that of the first embodiment, thus only the difference will be described below. The same reference numerals are given to the common configurations.

An arousal level determination device 2 of the second embodiment shown in FIG. 6 is different from the arousal level determination device 1 of the first embodiment shown in FIG. 1 in that the detection part 12 is replaced with a detection part 30, and vehicle information from the acquisition part 11 is inputted to the detection part 30 in addition to the decision part 13.

As shown in FIG. 7, the detection part 30 includes an actual measurement detection part 31, a first noise calculation part 32, a second noise calculation part 33, and a difference calculation part 34. First, an overview of the functions of these parts will be described.

The actual measurement detection part 31 has the same function as the detection part 12 of the first embodiment. That is, the actual measurement detection part 31 is configured to detect an amount of movement of the driver on the image, in other words, the amount of body movement detected based on the magnitude of the actual movement of the driver as the measured amount of body movement by performing differential processing on the image obtained from the imaging part 21.

The first noise calculation part 32 is configured to calculate the amount of body movement estimated as the magnitude of the movement caused by the driver's appropriate operation according to the surrounding situation of the vehicle based on the image obtained from the imaging part 21 as a first base amount of body movement.

The second noise calculation part 33 is configured to calculate the amount of body movement estimated as the magnitude of the movement of the driver due to the behavior of the vehicle based on the vehicle information inputted from the acquisition part 11 as a second base amount of body movement.

The difference calculation part 34 is configured to calculate the amount of body movement caused by sleepiness by subtracting the first base amount of body movement and the second base amount of body movement from the measured amount of body movement. That is, the first base amount of body movement and the second base amount of body movement form a baseline of body movement not caused by sleepiness.

As described above, the detection part 30 according to the second embodiment corrects the amount of body movement by subtracting the body movement that is not caused by the sleepiness that occurs during driving, such as the motion necessary for driving or the driver's motion unintentionally caused by the behavior of the vehicle as noise from the actual amount of body movement. As a result, the relationship between sleepiness during driving and the amount of body movement caused by the sleepiness is more appropriately extracted, and sleepiness estimation accuracy is improved.

Next, specific functions of the first noise calculation part 32, the second noise calculation part 33, and the difference calculation part 34 will be described.

The first noise calculation part 32 calculates the first base amount of body movement which is estimated as the magnitude of the movement caused by the driver's proper operation according to the surrounding situation of the vehicle.

For example, in a situation where another vehicle running on the next lane is overtaken, the driver's action to visually recognize the other vehicle, specifically, the face is directed to the other vehicle and then the face direction is changed to the front, is a proper operation according to the surrounding situation of the vehicle. Further, for example, in a situation where the vehicle passes by the side of another vehicle that is stopping on the road shoulder, the operation of the driver who visually recognizes the other vehicle is also an appropriate operation according to the surrounding situation of the vehicle. Although other vehicles are taken as an example here, the same applies to pedestrians and the like. The amount of body movement resulting from such a driver's motion becomes noise when calculating the amount of body movement resulting from sleepiness.

Therefore, the first noise calculation part 32 detects information regarding objects that may be visually recognized while the driver is driving, such as other vehicles or pedestrians around the vehicle, as an outside-vehicle environment information. Then, the first noise calculation part 32 calculates the amount of body movement estimated based on the outside-vehicle environment information as the first base amount of body movement.

Figure 8A:
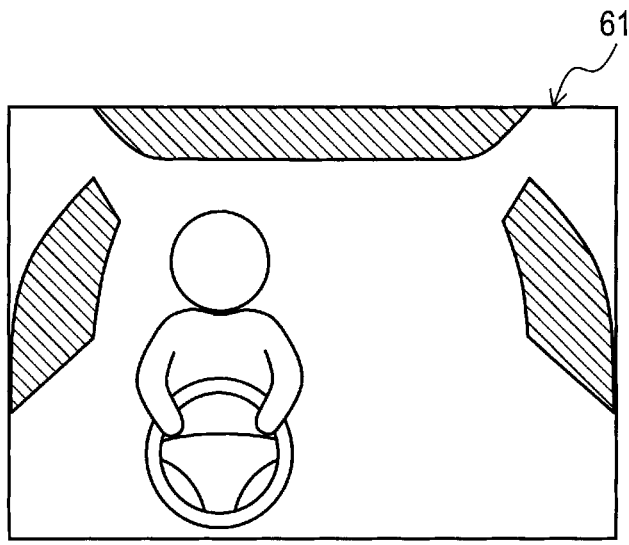
FIG. 8A is a diagram showing an example of an image acquired from an imaging part.

Specifically, the first noise calculation part 32 first obtains an image from the imaging part 21. For example, an image 61 shown in FIG. 8A is acquired.

Figure 8B:
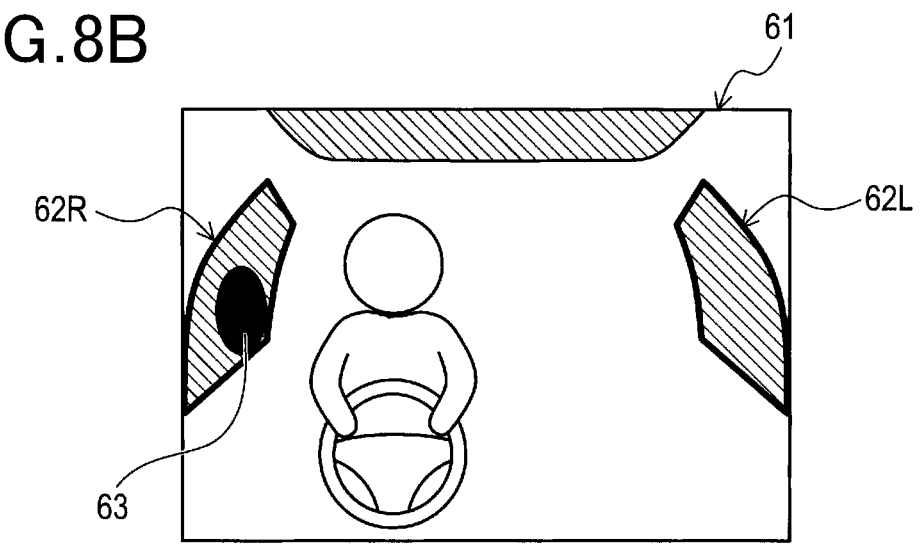
FIG. 8B is a diagram showing a detection range of outside-vehicle environment information in the image.

Next, the first noise calculation part 32 extracts an area in which the situation outside the vehicle can be identified on the obtained image as a detection range. In an example shown in FIG. 8B, the area within the frame of the left and right windows in the image 61 is extract as detection ranges 62R and 62L.

Next, the first noise calculation part 32 recognizes an object outside the vehicle from the image of the detection range. In the example shown in FIG. 8B, an object 63 is recognized from the environment outside the vehicle captured through the window on the right side of the driver.

Figure 8C:
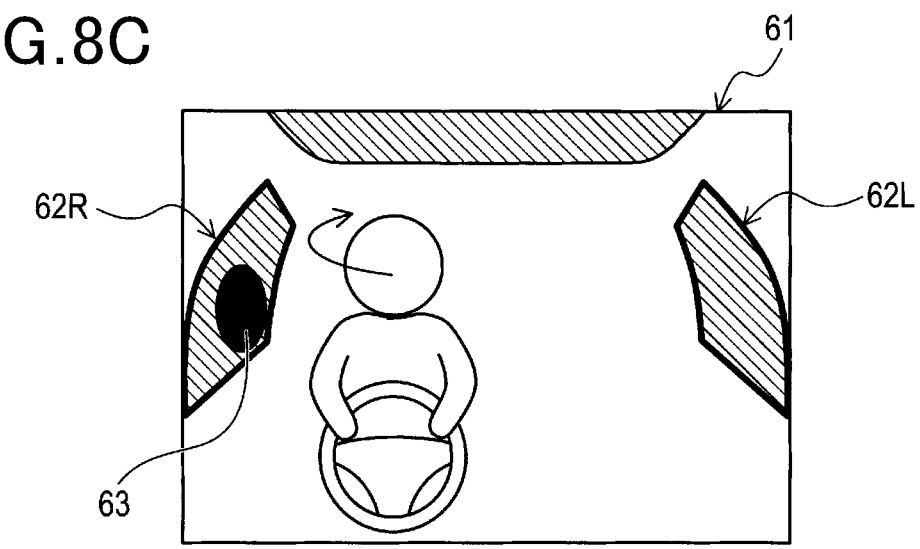
FIG. 8C is a diagram showing an example of an operation of a driver who visually recognizes an object.

Next, the first noise calculation part 32 calculates, from the recognized object, a first base amount of body movement estimated as the magnitude of the movement caused by the operation in which the driver recognizes the object during driving. In the example shown in FIG. 8C, the amount of body movement corresponding to the operation of the driver who visually recognizes the object 63 present on the right side of the vehicle is calculated. Here, a relationship between the object and the first basic amount of body movement can be learned in advance by machine learning based on the in-vehicle image data of the driver without sleepiness. For example, the correlation between an object recognized from an image captured under the same conditions as the imaging part 21 and the amount of body movement detected from the image is learned. The detection of the amount of body movement can be performed by the same method as the detection part 12 of the first embodiment. Further, as the image, it is possible to use a plurality of images continuously captured in a time series. In this case, the relative movement of the object relative to the vehicle is identified. For example, another vehicle traveling in the adjacent lane and another vehicle stopping at the road shoulder are identified.

Note that although an object outside the vehicle is recognized using the imaging part 21 which is a camera for imaging the driver from the front in the present embodiment, the object may be recognized using another device such as a camera for imaging the front of the vehicle and the surroundings of the vehicle or a radar that detects objects present around the vehicle, for example.

The second noise calculation part 33 calculates the amount of body movement estimated as the magnitude of an unintended movement of the driver due to the behavior of the vehicle as the second base amount of body movement.

Figure 9A:
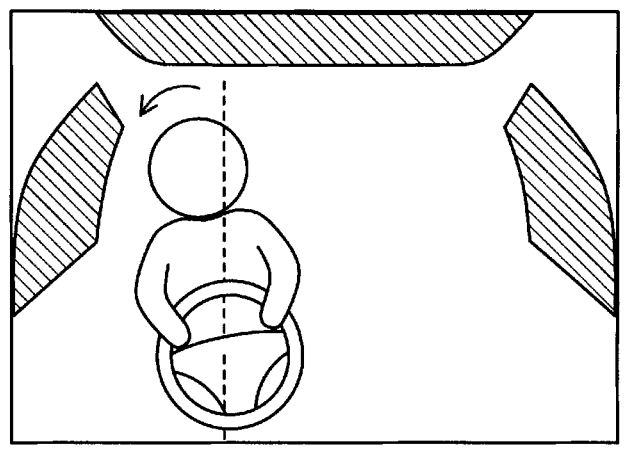
FIG. 9A is a diagram showing an example of movement of a body of the driver while traveling on a curved road.
Figure 9B:
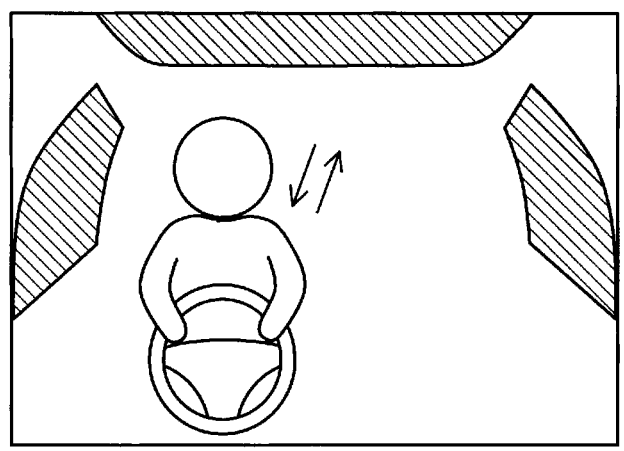
FIG. 9B is a diagram showing an example of movement of the body of the driver during deceleration or acceleration.

For example, under a situation where traveling on a curved road, as shown in FIG. 9A, the drivers body is inclined in the direction in which centrifugal force is applied. In addition, for example, during deceleration or acceleration, as shown in FIG. 9B, the drivers body tilts in the longitudinal (front-rear) direction. In particular, at the time of stopping after deceleration, the drivers body may vibrate so as to pinch forward. The amount of body movement resulting from such an unintended movement of the driver also becomes noise when calculating the amount of body movement resulting from sleepiness.

Therefore, the second noise calculation part 33 detects the behavior of the vehicle based on the vehicle information, and calculates the amount of body movement estimated as the magnitude of the movement of the driver due to the behavior of the vehicle as the second base amount of body movement.

Specifically, the second noise calculation part 33 first detects the behavior of the vehicle based on the vehicle information supplied by the acquisition part 11. For example, based on the vehicle speed detected by the vehicle speed sensor 22a and the steering angle detected by the steering angle sensor 22b, a state in which the vehicle is traveling on a curved road is detected as the behavior of the vehicle. Further, for example, based on the vehicle speed detected by the vehicle speed sensor 22a, the deceleration state or the acceleration state of the vehicle is detected as the behavior of the vehicle.

Next, the second noise calculation part 33 calculates, from the detected behavior, the second base amount of body movement estimated as the magnitude of the movement of the driver resulting from the behavior of the vehicle. Here, the relationship between the behavior of the vehicle and the second base amount of body movement can be learned in advance by machine learning based on the vehicle information and the in-vehicle image data of the driver without sleepiness. For example, the correlation between the behavior of the vehicle detected from the vehicle information detected under the same condition as the vehicle sensor 22 and the amount of body movement detected from the image captured under the same condition as the imaging part 21 is learned. The detection of the amount of body movement can be performed by the same method as the detection part 12 of the first embodiment. Moreover, as vehicle information, it is possible to use a plurality of pieces of vehicle information continuously detected in time series.

The difference calculation part 34 calculates the amount of body movement caused by sleepiness by subtracting the first base amount of body movement and the second base amount of body movement from the measured amount of body movement. In the present embodiment, the amount of body movement resulting from sleepiness is obtained according to the following formula (1).

$$C = A - \alpha_1 \times B_1 - \alpha_2 \times B_2 \tag{1}$$

Note that in the above equation (1), A is the measured amount of body movement, B1 is the first base amount of body movement, B2 is the second base amount of body movement, C is movement of the body due to sleepiness, and $\alpha_1$ and $\alpha_2$ are weight parameters.

[2-2. Processing]

Figure 3:
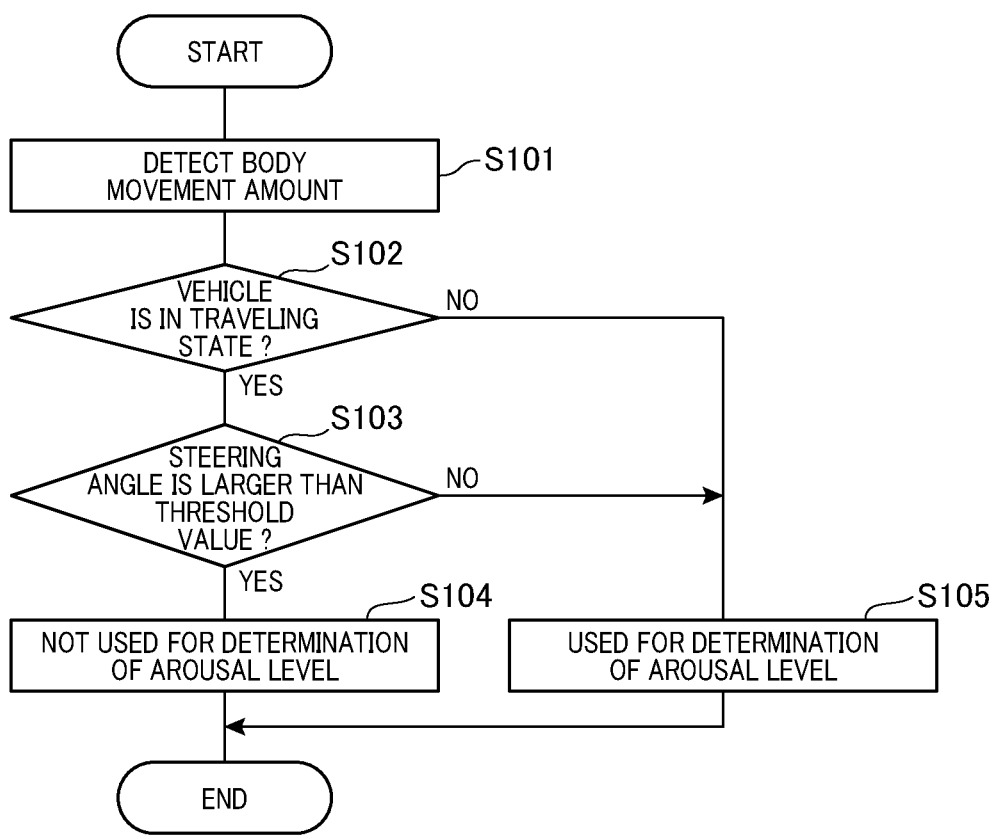
FIG. 3 is a diagram showing an example of a processing procedure in the arousal level determination device.

When comparing the processing executed by the arousal level determination device 2 of the second embodiment with the processing executed by the arousal level determination device 1 of the first embodiment, that is, the processing shown in FIGS. 3 and 4, it differs in that the processing shown in the flowchart of FIG. 10 is executed instead of the processing of S101 of FIG. 3.

When the processing of FIG. 10 is started, first, the arousal level determination device 2 acquires an image from the imaging part 21 in S301.

Subsequently, in S302, the arousal level determination device 2 receives vehicle information from the acquisition part 11.

Subsequently, in S303, the arousal level determination device 2 detects the measured amount of body movement A. S303 corresponds to the processing as the actual measurement detection part 31.

Subsequently, in S304, the arousal level determination device 2 calculates the first base amount of body movement B1. S304 corresponds to the processing as the first noise calculation part 32.

Subsequently, in S305, the arousal level determination device 2 calculates the second base amount of body movement B2. S305 corresponds to the processing of the second noise calculation part 33.

Subsequently, in S306, the arousal level determination device 2 calculates the amount of body movement C caused by sleepiness, and terminates the processing of FIG. 10. S306 corresponds to the processing of the difference calculation part 34.

[2-3. Effect]

According to the second embodiment described above, in addition to the same effects as the first embodiment, the following effects can be obtained.

(2a) The detection part 30 corrects the amount of body movement by subtracting the first base amount of body movement which is a value estimated as the magnitude of the movement caused by the driver's appropriate operation according to the surrounding situation of the vehicle from the measured amount of body movement detected based on the magnitude of the actual movement of the driver. Therefore, even in a situation where the driver operates the vehicle in accordance with the surrounding situation of the vehicle, the driver's arousal level decrease can be accurately detected.

(2b) The detection part 30 corrects the amount of body movement by subtracting the second base amount of body movement which is a value estimated as the magnitude of the movement of the driver caused by the behavior of the vehicle from the measured amount of body movement detected based on the magnitude of the actual movement of the driver. Therefore, even in a situation where the driver's body moves according to the behavior of the vehicle, the driver's arousal level decrease can be accurately detected.

3. Modification

The embodiments of the present disclosure have been described above, but the present disclosure can be variously modified and carried out without being limited to the above-mentioned embodiments.

(3a) In the above-described embodiments, although the decision part 13 decides whether the determination part 14 determines the arousal level based on the traveling state and the steering angle of the vehicle, the decision may be made based on either one of the information.

(3b) In the above-described embodiments, when deciding whether the determination part 14 has determined the arousal level, the decision part 13 uses the steering angle as the information of operation to the vehicle; however, the information of operation to the vehicle that the determination part 14 considers is not limited to this. For example, presence or absence of the turn signal operation may be used as the information of operation to the vehicle. That is, the decision part 13 may decide that the determination part 14 should not determine the arousal level for a predetermined period from when the turn signal operation by the driver is confirmed.

(3c) In the above-described embodiments, whether the vehicle is in the traveling state is determined based on the vehicle speed detected by the vehicle speed sensor 22a; however, whether the vehicle is in the traveling state may be determined based on an image obtained by imaging the outside of the vehicle, which is acquired from a drive recorder or the like.

(4d) In the above-described embodiments, it is decided not to determine the arousal level of the driver when the vehicle speed is equal to or less than zero; however, it may be decided not to determine the arousal level of the driver when the vehicle speed is equal to or less than a predetermined threshold value by considering that there may arise a possibility that the driver performs action other than the driving when the vehicle speed is low.

(3e) In the above-described embodiments, in the processing of FIG. 4, the arousal level of the driver is determined based on the change trends of the amount of body movements in the two periods, that is, in the past predetermined period t2 and in the predetermined period t1 one period before the predetermined period t2. When the arousal level of the driver is determined, the change trends of the amount of body movements in the three or more periods may be considered.

(3f) In the above-described embodiments, the decision part 13 decides whether to use the amount of body movement supplied by the detection part 12 for the determination of the arousal level in the determination part 14 and thereby decides whether the determination part 14 has determined the arousal level. However, the method of deciding whether the determination part 14 has determined the arousal level based on the amount of body movement is not limited to this. For example, the decision part 13 may be configured to decide whether the detection part 12 has detected the amount of body movement itself.

(3g) In the above-described embodiments, the accuracy of the determination of the arousal level may be increased by understanding the change trend of the amount of body movement according to a machine learning algorithm using a neural network such as Recurrent Neural Network (RNN) including Long Short-Term Memory (LSTM).

(3h) In the above-described embodiments, the accuracy of the determination of the arousal level may be increased by combining with other methods of determining the arousal level.

(3i) A plurality of functions of one component in the above-described embodiment may be realized by a plurality of components, or one function of one component may be realized by a plurality of components. In addition, a plurality of functions of a plurality of components may be realized by one component, or one function realized by a plurality of components may be realized by one component. Further, a part of the configuration of the above-described embodiment may be omitted. Furthermore, at least a part of the configuration of the above-described embodiment may be added to or replaced with another configuration of the above-described embodiment.

(3j) In addition to the above-mentioned arousal level determination device 1, the present disclosure can be also realized in various forms, such as a system using the arousal level determination device 1 as a component, a program for causing a computer to function as the arousal level determination device 1, a non-transitory tangible recording medium such as a semiconductor memory with its program recorded thereon, and an arousal level determination method.

What is claimed is:

1. An arousal level determination device that determines an arousal level of a driver driving a vehicle, the arousal level determination device comprising:

a detection part configured to detect an amount of body movement indicating a magnitude of movement of a body of the driver; and a determination part configured to determine the arousal level of the driver, wherein the determination part determines that the driver is in an initial stage of decline in the arousal level when the amount of body movement has a decreasing trend, and the determination part determines that the driver is in a progressive decline stage in the arousal level when the amount of body movement is changed from a decreasing trend to an increasing trend.

2. The arousal level determination device according to claim 1, wherein the detection part performs differential processing on an image obtained by imaging the driver along a time series to detect an amount of movement of the driver on the image as the amount of body movement.

3. The arousal level determination device according to claim 1, further comprising:

a decision part configured to decide whether the determination part has determined the arousal level of the driver based on the amount of body movement based on at least one of a traveling state information of the vehicle and an operation information for the vehicle.

4. The arousal level determination device according to claim 3, wherein the decision part decides not to determine the arousal level of the driver when a vehicle speed of the vehicle is equal to or less than a predetermined threshold value.

5. The arousal level determination device according to claim 3, wherein the decision part decides not to determine the arousal level of the driver when a steering angle of the vehicle is larger than a predetermined threshold value.

6. The arousal level determination device according to claim 1, wherein the detection part corrects the amount of body movement by subtracting a value estimated as a magnitude of a movement caused by a driver's appropriate operation according to surrounding situation of the vehicle from the amount of body movement detected based on a magnitude of an actual movement of the driver.

7. The arousal level determination device according to claim 1, wherein the detection part corrects the amount of body movement by subtracting a value estimated as a magnitude of a movement of the driver caused by a behavior of the vehicle from the amount of body movement detected based on a magnitude of an actual movement of the driver.

8. The arousal level determination device according to claim 1, wherein the progressive decline stage is a stage that occurs after the initial stage of decline.

9. A computer-implemented method for determining an arousal level of a driver driving a vehicle, the computer-implemented method comprising:

detecting an amount of body movement indicating a magnitude of movement of a body of the driver; and determining the arousal level of the driver, in which the driver is determined to be in an initial stage of decline in the arousal level based on the amount of body movement having a decreasing trend, and the driver is determined to be in a progressive decline stage in the arousal level based on the amount of body movement changing from a decreasing trend to an increasing trend.

10. The computer-implemented according to claim 9, wherein the progressive decline stage is a stage that occurs after the initial stage of decline.

* * * * *